United States Patent [19]

Yoshioka et al.

[11] Patent Number: 5,443,846
[45] Date of Patent: Aug. 22, 1995

[54] GRANULATED PREPARATIONS AND METHOD OF PRODUCING THE SAME

[75] Inventors: Minoru Yoshioka, Kyoto; Hidetoshi Horibe; Toshio Kashihara, both of Osaka, all of Japan

[73] Assignee: Takeda Chemical Industries, Ltd., Osaka, Japan

[21] Appl. No.: 217,770

[22] Filed: Mar. 25, 1994

Related U.S. Application Data

[63] Continuation of Ser. No. 908,865, Jul. 1, 1992, abandoned, which is a continuation of Ser. No. 692,354, Apr. 26, 1991, abandoned.

[30] Foreign Application Priority Data

Apr. 28, 1990 [JP] Japan .................... 2-114382

[51] Int. Cl.⁶ ................................ A61K 9/16
[52] U.S. Cl. ........................ 424/498; 424/502
[58] Field of Search ............ 424/469, 470, 502, 474

[56] References Cited

U.S. PATENT DOCUMENTS

| | | | |
|---|---|---|---|
| 3,936,391 | 2/1976 | Gabby et al. | 252/356 |
| 4,380,534 | 4/1983 | Fukui et al. | 424/498 |
| 4,386,120 | 5/1983 | Sato et al. | 427/213 |
| 4,751,241 | 6/1988 | Motoyama et al. | 514/532 |
| 4,755,387 | 7/1988 | Tzeghai et al. | 424/490 |
| 4,820,523 | 4/1989 | Shtohryn et al. | 424/469 |
| 4,842,863 | 6/1989 | Nishimura et al. | 424/498 |
| 4,894,233 | 1/1990 | Sharma et al. | 424/484 |
| 4,904,478 | 2/1990 | Walsdorf et al. | 424/468 |
| 4,935,245 | 6/1990 | Horn et al. | 424/489 |
| 4,935,246 | 6/1990 | Ahrens | 427/213 |
| 4,948,589 | 8/1990 | Iijima et al. | 424/490 |
| 5,017,383 | 5/1991 | Ozawa et al. | 427/213 |
| 5,169,645 | 12/1992 | Shukla et al. | 424/499 |

FOREIGN PATENT DOCUMENTS

| | | |
|---|---|---|
| 0368147 | 5/1990 | European Pat. Off. . |
| 48-34780 | 5/1973 | Japan . |
| 48-56577 | 8/1973 | Japan . |
| 58-214333 | 12/1983 | Japan . |
| 59-044327 | 3/1984 | Japan . |
| 1341515 | 12/1973 | United Kingdom . |
| 1513166 | 6/1978 | United Kingdom . |

OTHER PUBLICATIONS

Taiko Pharmaceutical, Chemical Abstracts, vol. 101 No. 16 p. 391 (1984) Abstract No. 137025k.

*Primary Examiner*—John C. Bleutge
*Assistant Examiner*—Amy L. Hulina
*Attorney, Agent, or Firm*—Wenderoth, Lind & Ponack

[57] ABSTRACT

Granulated preparations are provided by causing a granular, preferably spherical polyglycerol fatty acid ester having a melting poing of 40°–80° C. together with a powder for fluidized bed formation and heating the resulting fluidized mixture at a temperature in the vicinity of the melting point of the polyglycerol fatty acid ester. The powder may be contain as least one pharmacologically active ingredient. The polyglycerol fatty acid ester shows no crystal polymorphism and does not inactivate the pharmacologically active ingredient. Furthermore, the dissolution and release of the pharmacologically active ingredient can be controlled by varying the HLB of the polyglycerol fatty acid ester.

6 Claims, No Drawings

GRANULATED PREPARATIONS AND METHOD OF PRODUCING THE SAME

This application is a continuation of now abandoned application Ser. No. 07/908,865, filed Jul. 1, 1992, which in turn is a continuation of now abandoned application Ser. No. 07/692,354, filed Apr. 26, 1991.

FIELD OF THE INVENTION

This invention relates to granulated preparations which can suitably be used as powders, granules or fine granules or for tablet manufacture in the food, agrochemical, pharmaceutical and other fields and to a method of producing the same.

BACKGROUND OF THE INVENTION

For granulating powders, methods are known, for example the extrusion method, crushing method, spraying method, rolling method and fluidized-bed method. In granulating powders by these methods, a binder is generally used for intensifying the bonding among powder particles. In adding such a binder, an organic solvent or water is generally used. Thus, a solution of the binder in said organic solvent or water is added to said powder or, alternatively, the binder is added, in its powder form, to said powder, followed by addition of a solvent.

However, the use of organic solvents causes problems from the viewpoints of working environment, air pollution, safety and health, among others. On the other hand, the use of water makes it difficult to stably granulate compositions containing a medicinal substance which can be readily inactivated by water, for example a protein or antibiotic.

Among the granulation methods mentioned above, extrusion methods and crushing methods can granulate without using any solvent. However, the extrusion granulation method involves melting of the powders and the heat applied may readily inactivate the medicinal substances contained therein. This limits the range of application of said method. The granulation method essentially comprising crushing gives a broad grain size distribution to the granulated preparations and at the same time leads to dust (fine powder) formation. Furthermore, the granulated preparations produced by the crushing method have uneven grain surfaces and therefore, with them, it is difficult to achieve uniform coating, in particular uniform enteric coating.

On the other hand, with regard to the fluidized-bed granulation method, Japanese Patent laid open No. 34780/1973 discloses a granulation method which comprises fluidizing and heating a mixture of a plasticizable powder binder and an ingredient to be granulated, in a fluidized-bed reactor for causing adhesion or aggregation of said ingredient to or on the binder particle surface that has become sticky as a result of heating. Japanese Patent laid open No. 214333/1983 discloses granulated preparations produced by heating a mixture of a powder and a powdery/granular low-melting substance in a fluidized state for causing adhesion of the powder to the low-melting substance in the process of melting thereof. Japanese Patent Publication No. 20571/1979 discloses a method of granulating a powder tablet ingredient which comprises admixing the tablet ingredient with a powdery binder capable of melting or softening at a temperature inert to said ingredient, heating the resulting mixture in a fluidized bed at a temperature not lower than the melting point of the binder and then cooling the mixture to a temperature lower than the melting point of the binder without interrupting the air stream in the fluidized bed. These methods can give granulated preparations with relatively smooth surfaces in good yields in a solvent-free system without any step of crushing.

Japanese Patent laid open No. 56577/1973 discloses a method of producing granulated preparations with an average grain size of 20–60 mesh which comprises preparing pellet grains, 2–10 mm in diameter, in a dry state using 1 part by weight of a powdery carrier having a melting point of 45°–100° C. and 1–9 parts by weight of an active ingredient or an active ingredient-containing powder and crushing the resulting pellet grains at a temperature lower than the melting point of the powdery carrier by 5° to 25° C. using a crusher equipped with a knife rotating at a high speed. This method can give granulated preparations by utilizing the frictional heat generated on the occasion of pellet granulated preparation for melting the powdery carrier to thereby cause aggregation of the active ingredient, without severe dust formation.

Furthermore, Japanese Patent laid open No. 6869/1976 discloses a method of producing grains which comprises, in producing grains by drying and processing a mixture composed of a basic powdery substance and a meltable embedding substance under heating, causing said mixture to aggregate in a fluid mixer at a temperature not higher than the melting point of said embedding substance or at a temperature slightly higher than said melting point. In this method, the surface of the meltable embedding substance is rendered sticky by utilizing the actions of collision and friction as exerted on said meltable embedding substance in the step of mixing the mixture in the fluid mixer, whereby the basic powdery substance is allowed to aggregate on said surface without applying any external heat.

However, drug-containing granulated preparations produced by using those binders or low-melting substances that are described in the prior art documents cited above tend to show decreased drug dissolution or release due to the crystal polymorphism which the binders or the like exhibit. Furthermore, the drugs are readily inactivated upon interaction between the drugs and the binders and the like, hence the drugs cannot be stabilized for a prolonged period of time. Not only drugs but also various active ingredient-containing powders encounter these problems.

SUMMARY OF THE INVENTION

Accordingly, it is an object of the invention to provide granulated preparations capable of stably allowing dissolution and release of an active ingredient contained in the starting powder.

Another object of the invention is to provide granulated preparations capable of inhibiting the reaction of the active ingredient contained therein and thus stabilizing said active ingredient for a long period.

It is still another object of the invention to provide granulated preparations conducive to controlled dissolution and release of active ingredients.

A further object of the invention is to provide granulated preparations more close to spheres in form and capable of being coated uniformly and efficiently.

A still further object of the invention is to provide a method of producing granulated preparations having such advantageous characteristics as mentioned above in an efficient manner.

As a result of intensive investigations made by them in an attempt to achieve the above objects, the present inventors found that the use of polyglycerol fatty acid esters leads to stabilization of drug or active ingredient release and to marked inhibition of drug or active ingredient inactivation. The present invention has been completed based on these findings.

Thus, the invention provides granulated preparations produced by heating and fluidizing a granular polyglycerol fatty acid ester with a melting point of 40° to 80° C. and a powder.

The "polyglycerol fatty acid ester" is, for example, an ester of polyglycerol having a polymerization degree of 2 to 50 with a saturated or unsaturated higher fatty acid containing 8 to 40 carbon atoms. Preferred species of the polyglycerol fatty acid ester include, among others, tetraglycerol pentastearate, tetraglycerol monostearate, hexaglycerol pentastearate, hexaglycerol sesquistearate and decaglycerol monostearate. When the polyglycerol fatty acid ester is spherical, spherical granulated preparations are obtained and these are uniformly coated with enteric coating or other coating compositions.

The powder contains at least one of feeds, feed additives, foods, food additives, agrochemicals, drugs, excipients, binders, disintegrators, coloring agents, corrigents or flavors, adsorbents, preservatives, wetting agents, antistatic agents and disintegration retarders. Powders containing at least one pharmacologically active ingredient and powders each consisting of a pharmacologically active substance are preferably used.

The polyglycerol fatty acid ester contained in the granulated preparations mentioned above shows no crystal polymorphism, allows stable release and dissolution of the active ingredient of the powder and inhibits the inactivation of the active ingredient. The dissolution and release of the active ingredient from the granules can be adjusted by varying the HLB (hydrophile-lipophile balance) of the polyglycerol fatty acid ester. The HLB of the polyglycerol fatty acid ester can be selected within the range of 1 to 22. Alternatively, two or more polyglycerol fatty acid esters may be used for HLB adjustment.

The proportions of the polyglycerol fatty acid ester and powder are such that the powder amounts to 10–1,000 parts by weight per 100 parts by weight of the polyglycerol fatty acid ester.

The granulated preparations can be prepared by the fluidized-bed granulation method. According to this method, a granular polyglycerol fatty acid ester with a melting point of 40° to 80° C. and a powder are floated for fluidized bed formation, heating and floating the resulting mixture at a temperature in the neighborhood of the melting point of said polyglycerol fatty acid ester, preferably at a temperature from the melting point of said ester to a temperature lower by 5° C. than said melting point, for achieving granulation, and then cooling the resulting granulated preparation. Dropping of a molten polyglycerol fatty acid ester onto a rotating disk gives spheres of the polyglycerol fatty acid ester.

In cases where the polyglycerol fatty acid ester is a mixture, it does not show a distinct melting point but softens at a specific temperature in some instances. The term "melting point" as used herein includes, within the meaning thereof, the softening point of such mixture as well.

DETAILED DESCRIPTION OF THE INVENTION

The polyglycerol fatty acid ester may be a monoester, diester or polyester. Unlike hardened oils and the like, polyglycerol fatty acid esters show no crystal polymorphism and are further characterized in that they will hardly interact with drugs or other active ingredients.

Polyglycerol is a "polyhydric alcohol containing in each molecule thereof n (when cyclic) to n+2 (when straight-chained or branched) hydroxyl groups and n−1 (when straight-chained or branched) to n (when cyclic) ether bonds" ("Polyglycerol Esters" edited by Sakamoto Yakuhin Kogyo Co., Ltd., Japan, published May 2, 1986, page 12). Thus, for instance, compounds of the general formula

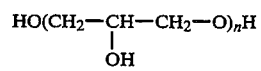

wherein n is the degree of polymerization and is an integer not less than 2, may be used. Generally, n is 2 to 50, preferably 2 to 20, more preferably 2 to 10. The polyglycerol may be branched as well as straight-chained.

Typical examples of such polyglycerols are diglycerol, triglycerol, tetraglycerol, pentaglycerol, hexaglycerol, heptaglycerol, octaglycerol, nonaglycerol, decaglycerol, pentadecaglycerol, eicosaglycerol and triacontaglycerol, among others. Among these, tetraglycerol, hexaglycerol, decaglycerol and the like are used most frequently.

The fatty acid includes, among others, saturated or unsaturated higher fatty acids containing 8 to 40, preferably 12 to 22, carbon atoms. As such fatty acids, there may be mentioned, for example, palmitic acid, stearic acid, oleic acid, linolic acid, linolenic acid, myristic acid, lauric acid, ricinolic acid, caprylic acid, capric acid and behenic acid. Among these fatty acids, stearic acid, oleic acid, lauric acid and ricinolic acid, for instance, are preferred.

As typical examples of the polyglycerol fatty acid ester, there may be mentioned decaglycerol monocaprylate, triglycerol dicaprylate, triglycerol dicaprate, tetraglycerol monolaurate, hexaglycerol monolaurate, decaglycerol monolaurate, tetraglycerol monooleate, hexaglycerol monooleate, decaglycerol monooleate, triglycerol dioleate, tetraglycerol dioleate, decaglycerol sesquioleate, tetraglycerol pentaoleate, hexaglycerol pentaoleate, decaglycerol decaoteate, heptaglycerol monolinolate, triglycerol dilinolate, tetraglycerol dilinolate, hexaglycerol dilinolate, tetraglycerol monostearate, hexaglycerol monostearate, decaglycerol monostearate, tetraglycerol tristearate, hexaglycerol tristearate, hexaglycerol sesquistearate, tetraglycerol pentastearate, hexaglycerol pentastearate, decaglycerol decastearate, tetraglycerol monopalmitate, hexaglycerol monopalmitate, decaglycerol monopalmitate, tetraglycerol tripalmitate, hexaglycerol tripalmitate, hexaglycerol sesquipalmitate, tetraglycerol pentapalmitate, hexaglycerol pentapalminate and decaglycerol decapalmitate, among others.

Preferred polyglycerol fatty acid esters are, for example, tetraglycerol pentastearate [e.g. PS-310 (trademark), Sakamoto Yakuhin Co., Japan], tetraglycerol monostearate [e.g. MS-310 (trademark), Sakamoto Yakuhin Co., Japan], hexaglycerol pentastearate [e.g. PS-500 (trademark), Sakamoto Yakuhin Co., Japan], hexaglycerol sesquistearate [e.g. SS-500 (trademark), Sakamoto Yakuhin Co., Japan] and decaglycerol monostearate.

These polyglycerol fatty acid esters may be used either singly or in the form of a mixture of two or more of them.

The polyglycerol fatty acid ester has a melting poing within the range of 40°–80° C., preferably about 40°–60° C.

The polyglycerol fatty acid ester generally has a molecular weight of 200to 5,000, preferably 300 to 2,000. It has an HLB (hydrophile-lipophile balance) of 1 to 22, preferably 1 to 15 and the dissolution of the active ingredient of the powder is controlled by adjusting the HLB. Thus, when a polyglycerol fatty acid ester having a high HLB value is used, the release and dissolution rate of the active ingredient from the granules increases while, with a polyglycerol fatty acid ester having a low HLB value, the release and dissolution rate of the active ingredient from the granules decreases. For adjustment of HLB, two or more polyglycerol fatty acid esters having dissimilar HLB values can be employed.

The polyglycerol fatty acid ester may be used in combination with a lipid. Usable as the lipid are water-insoluble substances acceptable to the intended use of the granulated preparations. The lipid should preferably have a softening point or melting point of 40° to 120° C., more preferably about 40° to 90° C.

As typical examples of the lipid, there may be mentioned hydrogenated oils derived from fats and oils, such as castor oil, cottonseed oil, soybean oil, rapeseed oil, beef tallow, etc.; beeswax, carnauba wax, spermaceti, lecithin, paraffin, microcrystalline wax; fatty acids, such as stearic acid and palmitic acid, and fatty acid salts, such as sodium and potassium salts; fatty alcohols, such as stearyl alcohol and cetyl alcohol; and glycerides. Preferred among these lipids are, for example, hydrogenated cottonseed oil, hardened castor oil, hardened soybean oil, carnauba wax, microcrystalline wax, stearic acid and stearyl alcohol and the like.

The lipid, when employed, is generally used in an amount of not more than 100 parts by weight per 100 parts by weight of the polyglycerol fatty acid ester and the amount thereof can suitably be selected within the range mentioned above.

In the practice of the invention, a granular, preferably spherical, polyglycerol fatty acid ester is used for causing a large amount of the powder to adhere to or be included in the polyglycerol fatty acid ester and for obtaining a granulated preparation corresponding in shape and grain size to the polyglycerol fatty acid ester. When a spherical polyglycerol fatty acid ester is used, the powder can be incorporated in large amounts into the granulated preparations by fluidized-bed granulation, for example in an amount such that the powder accounts for about 80% by weight of the whole granulated preparation and, furthermore, the granulated preparations obtained are relatively high in surface smoothness and spherical with a narrow grain size distribution. In some instances, the powder can amount to more than 80% by weight, for example about 85% by weight, of the whole granulated preparation. When a spherical polyglycerol fatty acid ester is used, the granulated preparations obtained are closer to the true spherical form and these granulated preparations are efficiently provided with a uniform coating, for example an enteric coating. Thus, the granulated preparations according to the invention may be coated ones, preferably enteric coated ones.

The spherical polyglycerol fatty acid ester can be prepared, for example by chilling. The spray chilling is effected by rotating a rotary disk, such as an aluminum disk, and dropping the polyglycerol fatty acid ester in a molten state obtained by heating over the melting point onto the rotating disk. The size of the rotary disk is not critical but is, for example, 5 to 100 cm, preferably about 10 to 20 cm, in diameter. The rate of revolution of the rotary disk and the rate of dropping of the molten polyglycerol fatty acid ester can be determined depending on the desired diameter of the granules and other factors. Generally, the rate of revolution of the rotary disk is 10 to 6,000 revolutions per minute, preferably 900 to 6,000 revolutions per minute, more preferably about 1,000 to 3,000 revolutions per minute. The dropping of the polyglycerol fatty acid ester can be conducted at a constant rate of flow, for example at a rate of 2 to 200 grams per minute, preferably about 5 to 100 grams per minute.

The grain size (grain diameter) of the granular polyglycerol fatty acid ester is not critical but can be selected depending on the desired grain size of the granulated preparations. Generally, it is within the range of 10 to 150 mesh, preferably about 25 to 100 mesh.

The powder to be granulated by using the granular polyglycerol fatty acid ester mentioned above can be selected depending on the intended use of the granulated preparations. Thus, various materials, for example feeds, foods, feed additives and food additives, such as vitamins, minerals and amino acids, pesticides, biocides, other agrochemicals, and antibiotics, chemotherapeutic agents and other medicinals which can be applied to animals including humans. Preferred powders contain at least one pharmacologically active substance, such as a medicinal or at least one agrochemically active substances. More preferred examples of powders are medicinals. When a powder containing or consisting of a pharmacologically active ingredient is used as the powder, the active ingredient can be stably released and dissolved since the above-mentioned polyglycerol fatty acid ester shows no crystal polymorphism. Furthermore, the interaction between said active ingredient and the polyglycerol fatty acid ester is not caused and the activity of the active ingredient can be maintained for a prolonged period of time.

Since, in the practice of the invention, granulation is effected by the fluidized-bed granulation method, the powder can be used irrespective of its melting point. The granular polyglycerol fatty acid ester may contain a portion of the powder composition, preferably a relatively low-melting powder ingredient, prior to fluidization and granulation. When a portion of the powder composition is incorporated into the granular polyglycerol fatty acid ester in advance, the powder ingredient can be incorporated thereinto in an amount which will not interfere with the granulation of the powder. Preferred powders contain at least one pharmacologically active ingredient. The pharmacologically active ingredient is not limited to any particular species. As is evident from the foregoing, medicinals having a relatively high melting point, medicinals having a relatively low melting point, peptides or proteins, etc. can equally be used.

As the drugs having a relatively higher melting point (e.g. 121° C. or above), there may be mentioned, for example, phenylpropanolamine hydrochloride, chlorpheniramine maleate, phenylephrine hydrochloride, theophylline, caffeine, procainamide hydrochloride, sulfanilamide, cephalexin, ampicillin, molsidomine, indomethacin, sulfisoxazole, sulfadiazine, diazepam, valproic acid, quinidine sulfate, aspirin, 3,4-dihydro-2,8-diisopropyl-3-thioxo-2H-1,4-benzoxazine-4-acetic acid, delapril hydrochloride, ipriflavone, trepibutone, N-ethyl-N-demethyl-8,9-anhydroerythromycin A 6,9-hemiketal, and 2,2'-[(2-aminoethyl)imino]diethanol bis(-butylcarbamate) dihydrochloride, cefotiam hexetil hydrochloride.

As the drugs with a relatively lower melting point (e.g. about 0°–120° C., preferably about 40°–120° C.), there may be mentioned, among others, isosorbide dinitrate, ketoprofen, cyclandelate and idebenone [i.e. 6-(10-hydroxydecyl)-2,3-dimethoxy-5-methyl-1,4-benzoquinone.

As the peptides or proteins, there may be mentioned, for example, insulin, vasopressin, interferons, IL-2, urokinase, aFGF and bFGF.

If necessary or where appropriate, the pharmacologically active ingredients mentioned above may be used in combination in the form of a mixture of two or more of them.

Further usable as the powder are, for example, excipients or carriers, such as lactose, corn starch, crystalline cellulose (e.g. Avicel ®), powdered sugar and magnesium stearate; binders such as starch, sucrose, gelatin, gum arabic powder, methylcellulose, carboxymethylcellulose sodium, hydroxypropylmethylcellulose and polyvinylpyrrolidone; disintegrators, such as carboxymethylcellulose calcium and L-hydroxypropylcellulose (hereinafter sometimes referred to also as L-HPC); coloring agents; corrigents; adsorbents; preservatives; wetting agents; antistatic agents; disintegration retarders; and so on. These powders are preferably used as diluents for the above-mentioned pharmacologically active ingredients.

The proportions of the above-mentioned polyglycerol fatty acid ester and the powder can be selected depending on the grain size desired of the granular preparations, the content of the pharmacologically active ingredient and other factors. Generally, however, the powder is used in an amount of 10 to 1,000 parts by weight, preferably 50 to 500 parts by weight, per 100 parts by weight of the polyglycerol fatty acid ester.

The granulation by heating and fluidizing can be carried out according to the conventional fluidized-bed granulation technique. The heating temperature in this granulation method is within the range of from the vicinity of the melting point of the polyglycerol fatty acid ester, preferably from the melting point thereof, to a temperature lower by 5° C. than said melting point. If the heating temperature is excessively high, the granules of the polyglycerol fatty acid ester tend to fuse together, giving a granulated preparation with a broad grain size distribution. If, conversely, the heating temperature is too low, it is difficult to attain granulation by means of the granular polyglycerol fatty acid ester.

The granulation can be carried out by floating the granular polyglycerol fatty acid ester and the powder for fluidized bed formation and heating under fluidization at an appropriate temperature. Whether the granulation is complete or not can be judged by the presence or absence of powder particles floating in the fluidized bed. After granulation, the granulated preparation is generally cooled under fluidization.

When granulation is carried out by such fluidized-bed granulation method, the use of an organic solvent is not required and, therefore, there is no risk of causing air pollution and the working environment can be improved. Furthermore, since the use of water is not required, the granulation method can be applied to a broad range of powders, inclusive of drugs unstable to water. In addition, the manufacturing process is simple and no special apparatus is required, hence the granulation can be conducted efficiently.

The granulated preparations of this invention as obtained in the above manner generally occur as fine granules or granules.

When examined under a scanning electron microscope, the granulated preparations according to the invention generally correspond in shape to the polyglycerol fatty acid ester used, apparently with the powder at least partially embedded in the granular polyglycerol fatty acid ester, preferably wholly included or integrated in said ester.

The granulated preparations according to the invention can be used as such, as powders or granulations, or subjected to tableting or some other processing to give tablets, sugar-coated tablets, capsules and so on. The granulated preparations according to the invention are particularly suited for use in manufacturing coated products, in particular enteric coated products.

The following examples are further illustrative of the invention but are by no means limitative of the scope thereof.

EXAMPLES

Example 1

Tetraglycerol monostearate (500 g; MS-310; Sakamoto Yakuhin Co., Japan) was added to 500 g of tetraglycerol pentastearate (PS-310; Sakamoto-Yakuhin Co., Japan), the mixture was heated at 90° C. for melting, and the molten mixture was dropped onto an aluminum disk (15 cm in diameter) rotating at 2,000 rpm at a rate of 20 grams per minute, whereby polyglycerol fatty acid ester spheres capable of passing through a 42-mesh sieve but incapable of passing through a 60-mesh sieve (hereinafter referred to briefly as "42/60M") were obtained.

A 50-g portion of the above 42/60M polyglycerol fatty acid ester mixture and 200 g of lactose were charged into a fluidized-bed granulator (Fuji Sangyo, model FD-3S) and the resultant mixture was heated and fluidized therein at a feed air temperature of 54° C. After confirmation of the disappearance of lactose particles floating in the fluidized bed, the heat source was stopped and the granulation product was cooled. The inlet air temperature mentioned above was sufficient for the polyglycerol fatty acid ester to soften. In the granules obtained, the lactose was adhering to or included in the spherical polyglycerol fatty acid ester. The granulated preparation obtained had the following grain size distribution:

| | |
|---|---|
| 12/24M | 1.3% by weight |
| 24/35M | 84.3% by weight |
| 35/60M | 5.6% by weight |
| 60/80M | 1.8% by weight |
| <80M | 7.0% by weight |

Example 2

A 60/80M polyglycerol fatty acid ester mixture was prepared in the same manner as in Example 1 except that the rate of disk revolution was adjusted to 3,000 rpm.

Using 50 g of the 60/80M polyglycerol fatty acid ester mixture obtained and 150 g of corn starch, the procedure of Example 1 was followed to give fine granules. The fine granules showed the following grain size distribution:

| | |
|---|---|
| 24/32M | 1.9% by weight |
| 32/48M | 84.5% by weight |
| 48/60M | 6.5% by weight |
| 60/80M | 6.5% by weight |
| <80M | 0.6% by weight |

Example 3

Using 300 g of the 60/80M polyglycerol fatty acid ester mixture obtained in Example 2 and 150 g of crystalline cellulose (Avicel, product of Asahi Chemical Industry Co., Ltd.), the procedure of Example 1 was followed to give granules. The granules showed the following grain size distribution:

| | |
|---|---|
| 24/32M | 32.6% by weight |
| 32/48M | 46.0% by weight |
| 48/60M | 10.5% by weight |
| 60/80M | 6.9% by weight |
| <80M | 4.0% by weight |

Example 4

Using 100 g of the 60/80M polyglycerol fatty acid ester mixture obtained in Example 2 and 500 g of atomizer-ground sucrose, the procedure of Example 1 was followed to give granules. The granules showed the following grain size distribution:

| | |
|---|---|
| 24/32M | 0.6% by weight |
| 32/48M | 69.8% by weight |
| 48/60M | 27.7% by weight |
| 60/80M | 1.5% by weight |
| <80M | 0.4% by weight |

Example 5

Using 100 g of the 60/80M polyglycerol fatty acid ester mixture obtained in Example 2, 260 g of corn starch and 40 g of N-ethyl-N-demethyl-8,9-anhydroerythromycin A 6,9-hemiketal, the procedure of Example 1 was followed to give fine granules. The fine granules showed the following grain size distribution:

| | |
|---|---|
| 24/32M | 1.3% by weight |
| 32/48M | 73.0% by weight |
| 48/60M | 20.5% by weight |
| 60/80M | 2.8% by weight |
| <80M | 2.4% by weight |

The drug in the fine granules obtained showed excellent stability.

Example 6

A 32/42M spherical polyglycerol fatty acid ester mixture was prepared in the same manner as in Example 1 except that the rate of disk revolution was adjusted to 1,000 rpm.

Using 100 g of the thus-obtained 32/42M polyglycerol fatty acid ester mixture and 100 g of L-HPC [containing 100 mg of bFGF (recombinant human basic fibroblast growth factor muteine CS23) produced as described in European Patent Specification No. 281822 in Example 1 thereof], the procedure of Example 1 was followed to give granules.

The bFGF in the granules obtained was excellent in stability.

Example 7

Using 50 g of the 60/80M polyglycerol fatty acid ester mixture obtained in Example 2 and 150 g of phenylpropanolamine hydrochloride, the procedure of Example 1 was followed to give fine granules.

The phenylpropanolamine hydrochloride in the fine granules obtained showed excellent stability.

Example 8

Using 50 g of the 60/80M polyglycerol fatty acid ester mixture obtained in Example 2 and 150 g of 2,2'-[(2-aminoethyl)imino]diethanol bis(butylcarbamate) dihydrochloride, the procedure of Example 1 was followed to give fine granules.

In the fine granules obtained, the 2,2'-[(2-aminoethyl)imino]diethanol bis(butylcarbamate) dihydrochloride was excellent in stability.

Example 9

To 498 g of tetraglycerol pentastearate (PS-310, product of Sakamoto Yakuhin Co., Japan) were added 498 g of tetraglycerol monostearate (MS-310, product of Sakamoto Yakuhin Co., Japan) and 4 g of idebenone, namely 6-(10-hydroxydecyl)-2,3-dimethoxy-5-methyl-1,4-benzoquinone. The mixture was melted by heating at 90° C. and the molten mixture was dropped onto an aluminum disk (15 cm in diameter) rotating at a rate of 3,000 rpm at a feed rate of 20 grams per minute, whereby a drug-containing polyglycerol fatty acid ester composition was obtained in the form of 60/80M spheres.

Using a 80 g portion of the thus-obtained polyglycerol fatty acid ester composition and 220 g of corn starch, the procedure of Example 1 was followed to give fine granules.

In the fine granules obtained, the idebenone was excellent in stability, as shown later herein in Test Example 1.

Comparative Example

Fine granules were produced in the same manner as in Example 9 except that 996 g of stearic acid (Wako Pure Chemical Industries, Ltd.) was used in lieu of the tetraglycerol pentastearate and monostearate.

Test Example 1

The fine granules obtained in Example 9 and the fine granules obtained in Comparative Example were stored at 40° C., 50° C. or 60° C. for the respective intervals given in Table 1 and then assayed for the drug (idebenone) by high-performance liquid chromatography (HPLC). The results are shown in Table 1. In the table, each value indicates the percent drug residue remaining at the time of assay, the idebenone content of the fine granules immediately after manufacture being taken as 100%.

TABLE 1

| Storage temperature | Storage period | Residual drug percentage | |
|---|---|---|---|
| | | Example 9 | Comparative example |
| 60° C. | 2 weeks | 100.0 | 75.8 |
| | 4 weeks | 100.0 | 57.5 |
| 50° C. | 2 weeks | 100.0 | 89.0 |
| | 4 weeks | 100.0 | 81.1 |
| 40° C. | 7 weeks | 100.0 | 95.5 |

As is evident from the data shown in Table 1, the fine granules produced by using the polyglycerol fatty acid ester showed high drug stability without drug inactivation as compared with the fine granules obtained by using stearic acid.

Test Example 2

A 200-g portion of the fine granules obtained in Example 5 were coated with 100 g of hydroxypropylmethylcellulose phthalate (HP-55S, product of Shin-Etsu Chemical Co., Ltd.), an enteric coating material. The enteric fine granules obtained were stored at 40° C. and drug dissolution rate measurements were carried out at timed intervals in the following manner.

The dissolution test was performed according to method 2 (paddle method) for dissolution test described in the 11th edition of the Japanese Pharmacopeia at a rate of paddle revolution of 100 rpm. The enteric fine granules were dissolved in 750 ml of 0.1N hydrochloric acid for 1 hour and then the pH was adjusted to 6.8 by addition of 250 ml of 0.2M trisodium phosphate. The time of addition of trisodium phosphate was taken as time 0 (zero). Samples were collected at timed intervals and assayed for drug concentration by HPLC. The initial drug content in the enteric fine granules was taken as 100% and the dissolution rate at each assay time was calculated as the percentage of the drug dissolved. The storage periods and dissolution times for the enteric fine granules as well as the results obtained are shown in Table 2.

TABLE 2

| Dissolution time (minutes) | | Drug dissolution percentage | | | | |
|---|---|---|---|---|---|---|
| | | 0 | 5 | 15 | 30 | 60 |
| Directly after manufacture | | 0 | 25.6 | 42.1 | 59.0 | 79.6 |
| Storage period | | | | | | |
| 40° C. | 1 week | 0 | 25.9 | 45.4 | 63.7 | 83.4 |
| | 2 weeks | 0 | 25.8 | 50.0 | 69.1 | 85.9 |
| | 4 weeks | 0 | 25.4 | 44.1 | 60.7 | 83.4 |
| | 12 weeks | 0 | 23.5 | 47.5 | 58.5 | 81.7 |

As is evident from the data given in Table 2, the enteric fine granules obtained in accordance with the invention retained their enteric property even after 12 weeks of storage at the acceleration test temperature of 40° C., as demonstrated by the dissolution data at pH 6.8 which were quite the same as those given by the enteric fine granules directly after manufacture.

Examples 10–12

Three 60/80M spherical polyglycerol fatty acid ester mixtures were prepared in the same manner as in Example 2 except that the ratio between tetraglycerol monostearate (MS-310, Sakamoto Yakuhin Co., Japan; HLB=8.4) and tetraglycerol pentastearate (PS-310, Sakamoto Yakuhin Co., Japan; HLB=2.6) was changed to MS-310/PS-310=500 g/500 g (Example 10), 300 g/700 g (Example 11) or 100 g/900 g (Example 12).

Using 150 g of each 60/80M polyglycerol fatty acid ester mixture thus obtained, 390 g of corn starch and 60 g of (±)-7-(3,5,6-trimethyl-1,4-benzoquinon-2-yl)-7-phenylheptanoic acid, the procedure of Example 1 was followed to give three fine granule preparations.

Test Example 3

The three fine granule preparations obtained in Examples 10–12 were subjected to dissolution testing. The test was performed essentially by method 2 (paddle method) for dissolution test as described in the 11th edition of the Japanese Pharmacopeia at a paddle revolution rate of 100 rpm. Samples were collected at timed intervals and the dissolution percentages were calculated from the filtrate absorbances. The results are shown in Table 3.

TABLE 3

| Dissolution time (minutes) | Drug dissolution percentage | | | | | | |
|---|---|---|---|---|---|---|---|
| | 5 | 10 | 15 | 20 | 30 | 45 | 60 |
| Fine granules | | | | | | | |
| Example 10 | 55.3 | 70.3 | 77.9 | 83.4 | 92.0 | 97.6 | 99.9 |
| Example 11 | 37.0 | 47.2 | 52.6 | 56.6 | 61.5 | 67.5 | 70.3 |
| Example 12 | 33.3 | 36.1 | 41.8 | 44.9 | 50.7 | 55.8 | 57.7 |

As is evident from the above results, the rate of drug dissolution from the fine granules could be adjusted as desired by varying the HLB of the polyglycerol fatty acid ester mixture.

What is claimed is:

1. A granulated preparation consisting essentially of a powder at least partially embedded or wholly included in a granular polyglycerol fatty acid ester having a melting point of 40° to 80° C. and a grain size of 10 to 150 mesh, wherein the powder constitutes 10–1,000 parts by weight per 100 parts by weight of the polyglycerol fatty acid ester, which preparation is obtained by heating the ester together with the powder up to a temperature in the vicinity of the melting or softening point of the ester without fusing the granular ester, while fluidizing, and which preparation is uncoated or coated with either a sugar or enteric coating.

2. A granulated preparation as claimed in claim 1, wherein the powder contains at least one member of the class consisting of feeds, feed additives, foods, food additives, agrochemicals, drugs or medicinal substances, excipients or carriers, binders, disintegrators, coloring agents, corrigents or flavoring agents, adsorbents, preservatives, wetting agents, antistatic agents and disintegration retarders.

3. A granulated preparation as claimed in claim 1, wherein the powder contains at least one pharmacologically active ingredient.

4. A granulated preparation as claimed in claim 1, wherein the powder is a pharmacologically active ingredient.

5. A granulated preparation as claimed in claim 3, wherein the pharmacologically active ingredient is a drug.

6. A granulated preparation as claimed in claim 4, wherein the pharmacologically active ingredient is a drug.

* * * * *